(12) United States Patent
O'Brien (10) Patent No.: US 7,993,358 B2
(45) Date of Patent: Aug. 9, 2011

(54) CUTTING BALLOON CATHETER HAVING INCREASED FLEXIBILITY REGIONS

(75) Inventor: Dennis O'Brien, Oceanside, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 157 days.

(21) Appl. No.: 12/409,680

(22) Filed: Mar. 24, 2009

(65) Prior Publication Data

US 2009/0192537 A1    Jul. 30, 2009

Related U.S. Application Data

(63) Continuation of application No. 11/057,300, filed on Feb. 11, 2005, now abandoned.

(51) Int. Cl.
*A61M 17/32* (2006.01)
*A61M 25/10* (2006.01)

(52) U.S. Cl. .................. 606/159; 604/103.08

(58) Field of Classification Search .............. 606/159, 606/170, 190, 191, 192, 194; 604/96.01, 604/103, 103.06, 103.08
See application file for complete search history.

(56) References Cited

U.S. PATENT DOCUMENTS

| | | | |
|---|---|---|---|
| 2,330,399 A | 9/1943 | Winder | |
| 2,486,056 A | 10/1949 | Oclassen | |
| 2,816,552 A | 12/1957 | Hoffman | |
| 3,050,066 A | 8/1962 | Koehn | |
| 3,174,851 A | 3/1965 | Buehler et al. | |
| 3,351,463 A | 11/1967 | Rozner et al. | |
| 3,409,016 A | 11/1968 | Foley | |
| 3,557,794 A | 1/1971 | VanPatten | |
| 3,635,223 A | 1/1972 | Klieman | |
| 3,749,085 A | 7/1973 | Willson et al. | |
| 3,753,700 A | 8/1973 | Harrison et al. | |
| 3,822,593 A | 7/1974 | Oudewaal | |
| 3,990,453 A | 11/1976 | Douvas et al. | |
| 4,018,231 A | 4/1977 | Wallace | |
| 4,140,126 A | 2/1979 | Choudhury | |
| 4,141,364 A | 2/1979 | Schultze | |
| 4,178,939 A | 12/1979 | Stephens | |
| 4,248,246 A | 2/1981 | Ikeda | |

(Continued)

FOREIGN PATENT DOCUMENTS

AU    74133/87 A    12/1987

(Continued)

OTHER PUBLICATIONS

Lary, B.G., "Experimental Maintenance of Life by Intravenous Oxygen, Preliminary Report," *Clinical Congress of the American College of Surgeons*, San Francisco, Nov. 5-9, 1951, pp. 30-35.

(Continued)

*Primary Examiner* — Anhtuan T Nguyen
*Assistant Examiner* — Amy Lang
(74) *Attorney, Agent, or Firm* — Seager, Tufte & Wickhem LLC (57) ABSTRACT

A cutting balloon catheter and method of using the same. The cutting balloon catheter may include a catheter shaft having a balloon coupled thereto. One or more cutting members or blades may be coupled to the balloon. The balloon may include one or more discrete points or areas of flexibility to enhance flexibility of the cutting balloon catheter. A break in the one or more cutting members may be aligned with the one or more discrete points of flexibility in the balloon.

20 Claims, 9 Drawing Sheets

U.S. PATENT DOCUMENTS

| | | | |
|---|---|---|---|
| 4,263,236 A | 4/1981 | Briggs et al. | |
| 4,273,128 A | 6/1981 | Lary | |
| 4,275,591 A | 6/1981 | Wand | |
| 4,276,874 A | 7/1981 | Wolvek et al. | |
| 4,292,974 A | 10/1981 | Fogarty et al. | |
| 4,346,698 A | 8/1982 | Hanson et al. | |
| 4,406,656 A | 9/1983 | Hattler et al. | |
| 4,416,267 A | 11/1983 | Garren et al. | |
| 4,444,186 A | 4/1984 | Wolvek et al. | |
| 4,449,532 A | 5/1984 | Storz | |
| 4,465,072 A | 8/1984 | Taheri | |
| 4,490,421 A | 12/1984 | Levy | |
| 4,572,186 A | 2/1986 | Gould et al. | |
| 4,573,470 A | 3/1986 | Samson et al. | |
| 4,574,781 A | 3/1986 | Chin | |
| 4,576,142 A | 3/1986 | Schiff | |
| 4,592,744 A | 6/1986 | Jagger et al. | |
| 4,601,713 A | 7/1986 | Fuqua | |
| 4,608,984 A | 9/1986 | Fogarty | |
| 4,627,436 A | 12/1986 | Leckrone | |
| 4,636,201 A | 1/1987 | Ambrose et al. | |
| 4,669,469 A | 6/1987 | Gifford, III et al. | |
| 4,681,092 A | 7/1987 | Cho et al. | |
| 4,685,458 A | 8/1987 | Leckrone | |
| 4,686,982 A | 8/1987 | Nash | |
| 4,696,667 A | 9/1987 | Masch | |
| 4,705,517 A | 11/1987 | DiPisa, Jr. | |
| 4,710,181 A | 12/1987 | Fuqua | |
| 4,723,549 A | 2/1988 | Wholey et al. | |
| 4,728,319 A | 3/1988 | Masch | |
| 4,738,666 A | 4/1988 | Fuqua | |
| 4,743,258 A | 5/1988 | Ikada et al. | |
| 4,747,405 A | 5/1988 | Leckrone | |
| 4,748,982 A | 6/1988 | Horzewski et al. | |
| 4,762,125 A | 8/1988 | Leiman et al. | |
| 4,762,130 A | 8/1988 | Fogarty et al. | |
| 4,771,776 A | 9/1988 | Powell et al. | |
| 4,781,186 A | 11/1988 | Simpson et al. | |
| 4,784,636 A | 11/1988 | Rydell | |
| 4,787,388 A | 11/1988 | Hofmann | |
| 4,790,813 A | 12/1988 | Kensey | |
| 4,793,348 A | 12/1988 | Palmaz | |
| 4,796,629 A | 1/1989 | Grayzel | |
| 4,799,479 A | 1/1989 | Spears | |
| 4,820,349 A | 4/1989 | Saab | |
| RE32,983 E | 7/1989 | Levy | |
| 4,846,174 A | 7/1989 | Willard et al. | |
| 4,846,344 A | 7/1989 | Bala | |
| 4,846,801 A | 7/1989 | Okuda et al. | |
| 4,867,157 A | 9/1989 | McGurk-Burleson et al. | |
| 4,881,547 A | 11/1989 | Danforth | |
| 4,886,061 A | 12/1989 | Fischell et al. | |
| 4,887,613 A | 12/1989 | Farr et al. | |
| 4,896,669 A | 1/1990 | Bhate et al. | |
| 4,906,244 A | 3/1990 | Pinchuk et al. | |
| 4,909,781 A | 3/1990 | Husted | |
| 4,921,483 A | 5/1990 | Wijay et al. | |
| 4,921,484 A | 5/1990 | Hillstead | |
| 4,930,341 A | 6/1990 | Euteneuer | |
| 4,935,190 A | 6/1990 | Tennerstedt | |
| 4,936,845 A | 6/1990 | Stevens | |
| 4,938,676 A | 7/1990 | Jackowski et al. | |
| 4,941,877 A | 7/1990 | Montano, Jr. | |
| 4,952,357 A | 8/1990 | Euteneuer | |
| 4,960,410 A | 10/1990 | Pinchuk | |
| 4,963,313 A | 10/1990 | Noddin et al. | |
| 4,966,604 A | 10/1990 | Reiss | |
| 4,979,951 A | 12/1990 | Simpson | |
| 4,983,167 A | 1/1991 | Sahota | |
| 4,986,807 A | 1/1991 | Farr | |
| 4,994,018 A | 2/1991 | Saper | |
| 4,994,072 A | 2/1991 | Bhate et al. | |
| RE33,561 E | 3/1991 | Levy | |
| 5,009,659 A | 4/1991 | Hamlin et al. | |
| 5,015,230 A | 5/1991 | Martin et al. | |
| 5,015,231 A | 5/1991 | Keith et al. | |
| 5,017,325 A | 5/1991 | Jackowski et al. | |
| 5,019,042 A | 5/1991 | Sahota | |
| 5,030,201 A | 7/1991 | Palestrant | |
| 5,037,392 A | 8/1991 | Hillstead | |
| 5,041,125 A | 8/1991 | Montano, Jr. | |
| 5,042,985 A | 8/1991 | Elliott et al. | |
| 5,047,040 A | 9/1991 | Simpson et al. | |
| 5,049,132 A | 9/1991 | Shaffer et al. | |
| 5,053,007 A | 10/1991 | Euteneuer | |
| 5,053,044 A | 10/1991 | Mueller et al. | |
| 5,071,424 A | 12/1991 | Reger | |
| 5,074,841 A | 12/1991 | Ademovic et al. | |
| 5,074,871 A | 12/1991 | Groshong | |
| 5,078,722 A | 1/1992 | Stevens | |
| 5,078,725 A | 1/1992 | Enderle et al. | |
| 5,084,010 A | 1/1992 | Plaia et al. | |
| 5,085,662 A | 2/1992 | Willard | |
| 5,087,246 A | 2/1992 | Smith | |
| 5,087,265 A | 2/1992 | Summers | |
| 5,100,424 A | 3/1992 | Jang et al. | |
| 5,100,425 A | 3/1992 | Fischell et al. | |
| 5,102,390 A | 4/1992 | Crittenden et al. | |
| 5,102,403 A | 4/1992 | Alt | |
| 5,116,318 A | 5/1992 | Hillstead | |
| 5,135,482 A | 8/1992 | Neracher | |
| 5,147,302 A | 9/1992 | Euteneuer et al. | |
| 5,152,773 A | 10/1992 | Redha | |
| 5,156,594 A | 10/1992 | Keith | |
| 5,156,610 A | 10/1992 | Reger | |
| 5,158,564 A | 10/1992 | Schnepp-Pesch et al. | |
| 5,176,693 A | 1/1993 | Pannek, Jr. | |
| 5,178,625 A | 1/1993 | Groshong | |
| 5,180,368 A | 1/1993 | Garrison | |
| 5,181,920 A | 1/1993 | Mueller et al. | |
| 5,192,291 A | 3/1993 | Pannek, Jr. | |
| 5,192,296 A | 3/1993 | Bhate et al. | |
| 5,195,970 A | 3/1993 | Gahara | |
| 5,196,024 A | 3/1993 | Barath | |
| 5,196,025 A | 3/1993 | Ranalletta et al. | |
| 5,209,749 A | 5/1993 | Buelna | |
| 5,209,799 A | 5/1993 | Vigil | |
| 5,224,945 A | 7/1993 | Pannek, Jr. | |
| 5,226,430 A | 7/1993 | Spears et al. | |
| 5,226,887 A | 7/1993 | Farr et al. | |
| 5,226,909 A | 7/1993 | Evans et al. | |
| 5,234,450 A | 8/1993 | Segalowitz | |
| 5,242,396 A | 9/1993 | Evard | |
| 5,248,311 A | 9/1993 | Black et al. | |
| 5,250,070 A | 10/1993 | Parodi | |
| 5,254,091 A | 10/1993 | Aliahmad et al. | |
| 5,295,959 A | 3/1994 | Gurbel et al. | |
| 5,295,995 A | 3/1994 | Kleiman | |
| 5,300,025 A | 4/1994 | Wantink | |
| 5,306,246 A | 4/1994 | Sahatjian et al. | |
| 5,308,323 A | 5/1994 | Sogawa et al. | |
| 5,308,356 A | 5/1994 | Blackshear, Jr. et al. | |
| 5,312,425 A | 5/1994 | Evans et al. | |
| 5,318,576 A | 6/1994 | Plassche, Jr. et al. | |
| 5,318,587 A | 6/1994 | Davey | |
| 5,320,634 A | 6/1994 | Vigil et al. | |
| 5,328,472 A | 7/1994 | Steinke et al. | |
| 5,336,178 A | 8/1994 | Kaplan et al. | |
| 5,336,234 A | 8/1994 | Vigil et al. | |
| 5,342,301 A | 8/1994 | Saab | |
| 5,342,307 A | 8/1994 | Euteneuer et al. | |
| 5,346,505 A | 9/1994 | Leopold | |
| 5,350,361 A | 9/1994 | Tsukashima et al. | |
| 5,366,472 A | 11/1994 | Hillstead | |
| 5,370,614 A | 12/1994 | Amundson et al. | |
| 5,372,601 A | 12/1994 | Lary | |
| 5,395,361 A | 3/1995 | Fox et al. | |
| 5,399,164 A | 3/1995 | Snoke et al. | |
| 5,403,334 A | 4/1995 | Evans et al. | |
| 5,409,454 A | 4/1995 | Fischell et al. | |
| 5,411,466 A | 5/1995 | Hess | |
| 5,411,477 A | 5/1995 | Saab | |
| 5,411,478 A | 5/1995 | Stillabower | |
| 5,415,654 A | 5/1995 | Daikuzono | |
| 5,417,653 A | 5/1995 | Sahota et al. | |
| 5,417,703 A | 5/1995 | Brown et al. | |
| 5,423,745 A | 6/1995 | Todd et al. | |

| | | | | | | |
|---|---|---|---|---|---|---|
| 5,425,711 | A | 6/1995 | Ressemann et al. | 6,165,167 | A | 12/2000 | Delaloye |
| 5,425,712 | A | 6/1995 | Goodin | 6,165,292 | A | 12/2000 | Abrams et al. |
| 5,437,659 | A | 8/1995 | Leckrone | 6,168,571 | B1 | 1/2001 | Solar et al. |
| 5,441,510 | A | 8/1995 | Simpson et al. | 6,179,851 | B1 | 1/2001 | Barbut et al. |
| 5,449,343 | A | 9/1995 | Samson et al. | 6,190,332 | B1 | 2/2001 | Muni et al. |
| 5,456,666 | A | 10/1995 | Campbell et al. | 6,193,686 | B1 | 2/2001 | Estrada et al. |
| 5,456,681 | A | 10/1995 | Hajjar | 6,213,957 | B1 | 4/2001 | Milliman et al. |
| 5,458,572 | A | 10/1995 | Campbell et al. | 6,217,549 | B1 | 4/2001 | Selmon et al. |
| 5,470,313 | A | 11/1995 | Crocker et al. | 6,217,567 | B1 | 4/2001 | Zadno-Azizi et al. |
| 5,478,319 | A | 12/1995 | Campbell et al. | 6,221,006 | B1 | 4/2001 | Dubrul et al. |
| 5,487,730 | A | 1/1996 | Marcadis et al. | 6,241,690 | B1 | 6/2001 | Burkett et al. |
| 5,490,839 | A | 2/1996 | Wang et al. | 6,254,550 | B1 | 7/2001 | McNamara et al. |
| 5,496,308 | A | 3/1996 | Brown et al. | 6,258,108 | B1 | 7/2001 | Lary |
| 5,507,760 | A | 4/1996 | Wynne et al. | 6,283,743 | B1 | 9/2001 | Traxler et al. |
| 5,507,761 | A | 4/1996 | Duer | 6,306,105 | B1 | 10/2001 | Rooney et al. |
| 5,522,818 | A | 6/1996 | Keith et al. | 6,306,151 | B1 | 10/2001 | Lary |
| 5,522,825 | A | 6/1996 | Kropf et al. | 6,309,399 | B1 | 10/2001 | Barbut et al. |
| 5,538,510 | A | 7/1996 | Fontirroche et al. | 6,319,242 | B1 | 11/2001 | Patterson et al. |
| 5,542,924 | A | 8/1996 | Snoke et al. | 6,344,029 | B1 | 2/2002 | Estrada et al. |
| 5,545,132 | A | 8/1996 | Fagan et al. | 6,355,016 | B1 | 3/2002 | Bagaoisan et al. |
| 5,549,556 | A | 8/1996 | Ndondo-Lay et al. | 6,383,146 | B1 | 5/2002 | Klint |
| 5,554,121 | A | 9/1996 | Ainsworth et al. | 6,387,075 | B1 | 5/2002 | Stivland et al. |
| 5,556,405 | A | 9/1996 | Lary | 6,394,995 | B1 | 5/2002 | Solar et al. |
| 5,556,408 | A | 9/1996 | Farhat | 6,398,798 | B2 | 6/2002 | Selmon et al. |
| 5,569,195 | A | 10/1996 | Saab | 6,409,863 | B1 | 6/2002 | Williams et al. |
| 5,569,277 | A | 10/1996 | Evans et al. | 6,425,882 | B1 | 7/2002 | Vigil |
| 5,571,087 | A | 11/1996 | Ressemann et al. | 6,428,552 | B1 | 8/2002 | Sparks |
| 5,616,149 | A | 4/1997 | Barath | 6,458,076 | B1 | 10/2002 | Pruitt |
| 5,628,761 | A | 5/1997 | Rizik | 6,471,673 | B1 | 10/2002 | Kasterhofer |
| 5,643,209 | A | 7/1997 | Fugoso et al. | 6,471,713 | B1 | 10/2002 | Vargos et al. |
| 5,643,278 | A | 7/1997 | Wijay | 6,533,754 | B1 | 3/2003 | Hisamatsu et al. |
| 5,643,296 | A | 7/1997 | Hundertmark et al. | 6,544,224 | B1 | 4/2003 | Steese-Bradley |
| 5,645,529 | A | 7/1997 | Fagan et al. | 6,544,276 | B1 | 4/2003 | Azizi |
| 5,649,941 | A | 7/1997 | Lary | 6,562,062 | B2 | 5/2003 | Jenusaitis et al. |
| 5,658,311 | A | 8/1997 | Baden | 6,565,527 | B1 | 5/2003 | Jonkman et al. |
| 5,662,671 | A | 9/1997 | Barbut et al. | 6,565,588 | B1 | 5/2003 | Clement et al. |
| 5,669,920 | A | 9/1997 | Conley et al. | 6,602,265 | B2 | 8/2003 | Dubrul et al. |
| 5,681,336 | A | 10/1997 | Clement et al. | 6,632,231 | B2 * | 10/2003 | Radisch, Jr. .................. 606/159 |
| 5,697,944 | A | 12/1997 | Lary | 6,730,105 | B2 | 5/2004 | Shiber |
| 5,713,913 | A | 2/1998 | Lary et al. | 6,746,463 | B1 | 6/2004 | Schwartz |
| 5,718,684 | A | 2/1998 | Gupta | 6,776,771 | B2 | 8/2004 | van Moorlegem et al. |
| 5,720,724 | A | 2/1998 | Ressemann et al. | 7,303,572 | B2 | 12/2007 | Melsheimer et al. |
| 5,728,123 | A | 3/1998 | Lemelson et al. | 2002/0010489 | A1 | 1/2002 | Grayzel et al. |
| 5,730,698 | A | 3/1998 | Fischell et al. | 2002/0082592 | A1 | 6/2002 | Lary |
| 5,743,875 | A | 4/1998 | Sirhan et al. | 2003/0032973 | A1 | 2/2003 | Jenusaitis et al. |
| 5,759,191 | A | 6/1998 | Barbere | 2003/0040770 | A1 | 2/2003 | Radisch, Jr. |
| 5,769,819 | A | 6/1998 | Schwab et al. | 2003/0144677 | A1 | 7/2003 | Lary |
| 5,769,865 | A | 6/1998 | Kermode et al. | 2003/0153870 | A1 | 8/2003 | Meyer et al. |
| 5,792,105 | A | 8/1998 | Lin et al. | 2003/0163148 | A1 | 8/2003 | Wang et al. |
| 5,792,150 | A | 8/1998 | Pratt et al. | 2004/0034384 | A1 | 2/2004 | Fukaya |
| 5,792,158 | A | 8/1998 | Lary | 2004/0098018 | A1 | 5/2004 | Radisch, Jr. |
| 5,797,935 | A | 8/1998 | Barath | 2004/0122457 | A1 | 6/2004 | Weber |
| 5,800,450 | A | 9/1998 | Lary et al. | 2004/0127920 | A1 | 7/2004 | Radisch, Jr. |
| 5,820,594 | A | 10/1998 | Fontirroche et al. | 2004/0230178 | A1 | 11/2004 | Wu |
| 5,824,173 | A | 10/1998 | Fontirroche et al. | 2004/0243156 | A1 | 12/2004 | Wu et al. |
| 5,827,201 | A | 10/1998 | Samson et al. | 2004/0243158 | A1 | 12/2004 | Konstantino et al. |
| 5,827,225 | A | 10/1998 | Ma Schwab | 2005/0038383 | A1 | 2/2005 | Kelley et al. |
| 5,827,310 | A | 10/1998 | Mann et al. | 2005/0240148 | A1 | 10/2005 | Cheves et al. |
| 5,860,954 | A | 1/1999 | Ropiak | 2005/0240212 | A1 | 10/2005 | McAuley et al. |
| 5,895,402 | A | 4/1999 | Hundertmark et al. | 2006/0106412 | A1 | 5/2006 | Crow et al. |
| 5,921,958 | A | 7/1999 | Ressemann et al. | 2006/0106413 | A1 | 5/2006 | Bence et al. |
| 5,931,819 | A | 8/1999 | Fariabi | 2006/0149308 | A1 * | 7/2006 | Melsheimer et al. ......... 606/192 |
| 5,954,740 | A | 9/1999 | Ravenscroft et al. | | | | |
| 5,993,469 | A | 11/1999 | McKenzie et al. | | | FOREIGN PATENT DOCUMENTS | |
| 5,997,557 | A | 12/1999 | Barbut et al. | DE | | 1 170 586 | 5/1964 |
| 6,010,521 | A | 1/2000 | Lee et al. | DE | | 31 24 198 A1 | 4/1982 |
| 6,013,055 | A | 1/2000 | Bampos et al. | DE | | 34 00 416 A1 | 7/1985 |
| 6,022,359 | A * | 2/2000 | Frantzen ....................... 606/108 | DE | | 34 02 573 A1 | 8/1985 |
| 6,024,722 | A | 2/2000 | Rau et al. | DE | | 35 19 626 A1 | 12/1986 |
| 6,030,371 | A | 2/2000 | Pursley | DE | | 100 10 467 A1 | 9/2001 |
| 6,039,699 | A | 3/2000 | Viera | EP | | 0 291 170 A1 | 11/1988 |
| 6,048,350 | A | 4/2000 | Vrba | EP | | 0 414 350 A1 | 2/1991 |
| 6,066,149 | A | 5/2000 | Samson et al. | EP | | 0 784 966 B1 | 7/1997 |
| 6,068,623 | A | 5/2000 | Zadno-Azizi et al. | EP | | 0 792 656 131 | 9/1997 |
| 6,110,192 | A | 8/2000 | Ravenscroft et al. | EP | | 1 270 040 A1 | 2/2003 |
| 6,117,153 | A | 9/2000 | Lary et al. | GB | | 1 547 328 | 6/1979 |
| 6,139,510 | A | 10/2000 | Palermo | GB | | 2 078 114 A | 1/1982 |
| 6,142,975 | A | 11/2000 | Jalisi et al. | WO | | WO 90/07909 A1 | 7/1990 |
| 6,165,140 | A | 12/2000 | Ferrera | WO | | WO 91/17714 A1 | 11/1991 |

| WO | WO 92/19306 A1 | 11/1992 |
| WO | WO 95/00198 A1 | 1/1995 |
| WO | WO 95/05860 A1 | 3/1995 |

OTHER PUBLICATIONS

Lary, Banning G., "A Method to Create and Correct Stenosis of a Coronary Artery," *Archives of Surgery*, Nov. 1966, vol. 93, pp. 828-830.

Lary, Banning G., "An Epicaridal Purse String Suture for Closing Coronary Arteriotomy," The American Surgeon, Mar. 1967, vol. 33, No. 3, pp. 213-214.

Lary, Banning G., "Coronary Artery Incision and Dilation," *Archives of Surgery*, Dec. 1980, vol. 115, pp. 1478-1480.

Lary, Banning G., "Coronary Artery Resection and Replacement by a Blood Conduit," *Surgery*, Apr. 1969, vol. 65, No. 4, pp. 584-589.

Lary, Banning G., "Effect of Endocardial Incisions on Myocardial Blood Flow," *Archives of Surgery*, Sep. 1963, vol. 87, pp. 424-427.

Lary, Banning G., "Method for Increasing the Diameter of Long Segments of the Coronary Artery," *The American Surgeon*, Jan. 1966, vol. 32, No. 1, pp. 33-35.

Lary, Banning G., "Onlay Vein Graft for the Correction of Coronary Artery Obstruction," *Surgery*, Apr. 1966, vol. 59, No. 4, pp. 547-551.

Lary, Banning G., et al., "Surgery for Coronary Artery Disease," *Nursing Clinics of North America*, Sep. 1967, vol. 2, No. 3, pp. 537-542.

Lary, Banning G., et al., "A Method for Creating a Coronary-Myocardial Artery," *Surgery*, Jun. 1966, vol. 59, No. 6, pp. 1061-1064.

Lary, Banning G., et al., "Experimental Vein Angioplasty of the Circumflex Coronary Artery," *Journal of Surgical Research*, Sep. 1974, vol. 17, No. 3, pp. 210-214.

Lary, Banning G., et al., "Myocardial Revascularization Experiments Using the Epicardium," *Archives of Surgery*, Jan. 1969, vol. 98, pp. 69-72.

Lary, Banning G., et al., "The 'Coronary Myocardial Artery' for Coronary Artery Disease," *Diseases of the Chest*, Apr. 1996, vol. 49, No. 4, pp. 412-419.

* cited by examiner

CUTTING BALLOON CATHETER HAVING INCREASED FLEXIBILITY REGIONS

CROSS REFERENCE TO RELATED APPLICATIONS

This application is a continuation of U.S. application Ser. No. 11/057,300, filed Feb. 11, 2005, now abandoned, the entire disclosure of which is incorporated herein by reference.

TECHNICAL FIELD

The present invention pertains to angioplasty and angioplasty balloon catheters. More particularly, the present invention pertains to angioplasty balloon catheters that include one or more cutting edges coupled to an angioplasty balloon having increased flexibility.

BACKGROUND

Heart and vascular disease are major problems in the United States and throughout the world. Conditions such as atherosclerosis result in blood vessels becoming blocked or narrowed. This blockage can result in a lack of oxygenation to the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter may be advanced through a vasculature over a guidewire so that the balloon is positioned at a target location. The balloon may then be inflated in a manner such that the restriction in the vessel is opened.

One of the major obstacles in treating coronary artery disease and/or treating blocked blood vessels is re-stenosis. Evidence has shown that cutting the stenosis, for example with an angioplasty balloon equipped with a cutting edge, during treatment can reduce incidence of re-stenosis. Additionally, cutting the stenosis may reduce trauma at the treatment site and/or reduce the trauma to adjacent healthy tissue. Cutting blades may also be beneficial additions to angioplasty procedures when the targeted occlusion is hardened or calcified. It is believed typical angioplasty balloons, alone, may not be able to sufficiently expand at least a portion of these hardened lesions. Thus, angioplasty balloons equipped with cutting edges have been developed in an attempt to enhance angioplasty treatments. There is an ongoing need for improved angioplasty devices, including cutting angioplasty balloons, and improved methods of treating intravascular stenoses and occlusions.

SUMMARY

The invention generally relates to improved angioplasty devices for treating vascular abnormalities, such as a stenosis. In at least some embodiments, an exemplary angioplasty device may include a catheter shaft having a balloon coupled thereto. One or more cutting members or blades may be coupled to the balloon. The balloon may include one or more discrete points or areas of flexibility to improve the flexibility of the balloon during delivery, deployment, and/or withdrawal of an angioplasty device. Such discrete points or areas of flexibility may include one or more creases, folds, reduced diameter portions, less expandable portions, regions of reduced wall thickness, and the like, formed in a portion of the balloon.

Accordingly, one exemplary embodiment of the invention is a cutting balloon catheter including a balloon having one or more generally circumferentially extending creases formed in the balloon wall. One or more cutting members may be coupled to the balloon such that breaks in the cutting members, or segments thereof, are aligned with the one or more creases to impart greater flexibility to the balloon portion.

Another embodiment of the invention includes an atherotomy device for the treatment of coronary artery disease. The atherotomy device includes a plurality of cutting edges or atherotomes coupled to an inflatable balloon. The atherotomes may be segmented to provide flexibility. The balloon may also include at least one circumferential crease to improve the flexibility of the balloon during an atherotomy procedure. The flexibility provided by the at least one circumferential crease and/or the segmented atherotomes allows the cutting balloon to more readily conform to the curvature of a vascular passageway. Balloons not having such flexibility may tend to straighten as they are inflated in a curved vascular pathway, thereby placing uneven pressure on the wall of the vessel and subjecting unnecessary trauma to the vessel.

BRIEF DESCRIPTION OF THE DRAWINGS

The invention may be more completely understood in consideration of the following detailed description of various embodiments of the invention in connection with the accompanying drawings, in which.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. Unless indicated otherwise, the term "about" generally refers to a range of numbers that one of skill in the art would consider equivalent to the recited value (i.e., having the same function or result). In many instances, the term "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5). As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Figure 1:
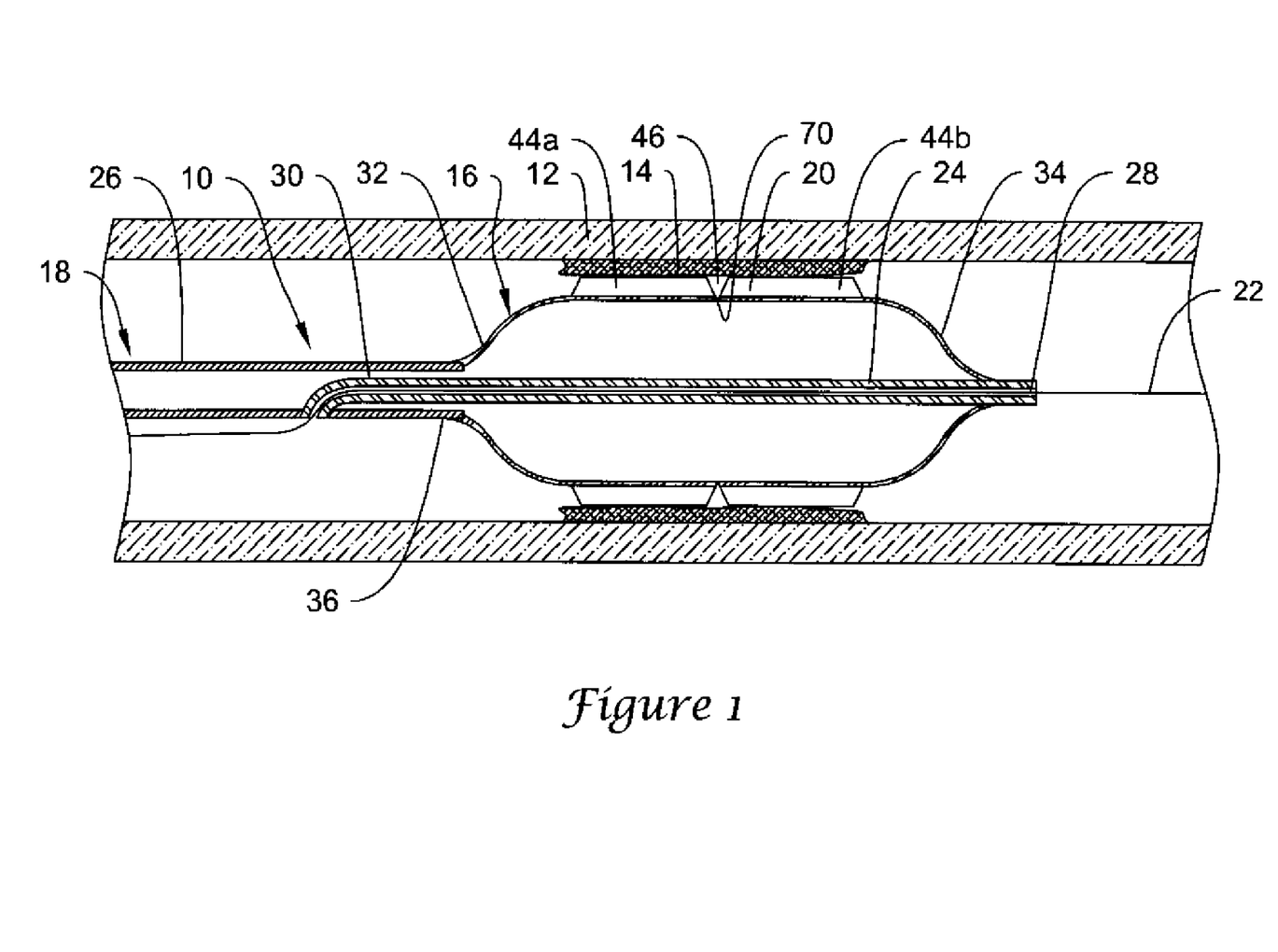
FIG. 1 is a partial cross-sectional view of a representative cutting balloon catheter in accordance with an embodiment of the invention.

FIG. 1 is a partial cross-sectional side view of an exemplary catheter 10 disposed in a blood vessel 12 and positioned adjacent an intravascular lesion 14. Catheter 10 may include a balloon 16 coupled to a catheter shaft 18. One or more cutting members or blades 20 may be coupled to balloon 16. In general, catheter 10 may be advanced over a guidewire 22, through the vasculature, to a target area. Balloon 16 can then be inflated to expand lesion 14, and cutting members 20 may cut lesion 14. The target area may be within any suitable peripheral, cardiac or other vessel lumen location.

Cutting members 20 may vary in number, position, and arrangement about balloon 16. For example, catheter 10 may include one, two, three, four, five, six, or more cutting members 20 that are disposed at any position along balloon 16 and in a regular, irregular, or any other suitable pattern. The pattern can include a generally helical orientation of the cutting members 20. Catheter 10 may include a plurality of cutting members 20 placed equidistantly about balloon 16 extending generally longitudinally. In general, cutting members 20 may be configured to provide variable flexibility or otherwise vary the flexibility of catheter 10. Increasing the flexibility of cutting members 20, balloon 16, and/or catheter 10 may be desirable, for example, because it may improve the tracking ability and general deliverability of catheter 10 through the often tortuous anatomy. Additionally, increasing the flexibility may allow catheter 10 to be navigable to a larger number of intravascular locations, including some that may not be readily reachable by other, less flexible, cutting balloon catheters. In general, the enhanced flexibility may be the result of a structural feature of cutting members 20, a structural modification to cutting members 20, and/or a structural feature of the cutting balloon 16. For example, cutting members 20 may include a first section 44a, a second section 44b, and a gap or break 46 disposed between first section 44a and second section 44b. Break 46 may be configured to provide a region of flexibility such as a space between first section 44a and second section 44b. In some embodiments, break 46 may be defined by a downward deflection or slot that is formed in the cutting surface of cutting member 20. Alternatively, break 46 may not be a physical gap between first section 44a and second section 44b, but rather break 46 may be a region of cutting member 20 having a reduced wall thickness or may comprise a material having an increased flexibility relative to the material of first and second sections 44a, 44b. Break 46 also may comprise an exogenous connector that is connected to both first section 44a and second section 44b in order to bridge sections 44a, 44b. Separation of sections 44a, 44b can increase the flexibility of cutting member 20 and/or the overall flexibility of catheter 10.

Cutting members 20 may be made from any suitable material such as a metal, metal alloy, polymer, metal-polymer composite, and the like, or any other suitable material. For example, cutting members 20 may be made from stainless steel such as 304V, 304L, or 316L stainless steel. In other embodiments, cutting member 20 can be made from a glass/KEVLAR® complex material such as ARAMAT®, which is commercially available. Some examples of other suitable materials are listed below in relation to balloon 16 and shaft 18.

Balloon 16 may be made from typical angioplasty balloon materials including polymers such as polyethylene terephthalate (PET), polyetherimide (PEI), polyethylene (PE), etc. Some other examples of suitable polymers, including lubricious polymers, may include polytetrafluoroethylene (PTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), polyether-ester (for example, a polyether-ester elastomer such as ARNITEL® available from DSM Engineering Plastics), polyester (for example, a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example, available under the trade name PEBAX®), silicones, Marlex high-density polyethylene, Marlex low-density polyethylene, linear low density polyethylene (for example, REXELL®), polyetheretherketone (PEEK), polyimide (PI), polyphenylene sulfide (PPS), polyphenylene oxide (PPO), poly(ethylene naphthalenedicarboxylate) (PEN), polysulfone, nylon, perfluoro(propyl vinyl ether) (PFA), other suitable materials, or mixtures, combinations, copolymers thereof, polymer/metal composites, and the like. In some embodiments, it may be desirable to use a relatively non-compliant balloon or a balloon including high modulus or generally stiffer materials so as to reduce balloon elongation. The above list of materials includes some examples of higher modulus materials. Some other examples of stiffer materials include polymers blended with liquid crystal polymer (LCP) as well as the materials listed above. For example, the mixture can contain up to about 5% LCP. Balloon 16 may include fiber, particulate material, or other reinforcing filaments. For example, balloon 16 may comprise a nanocomposite polymer material.

Balloon 16 may be configured so that it includes one or more "wings" or wing-shaped regions when balloon 16 is deflated. These wings may appear as a plurality of alternating inward and outward radial deflections in balloon 16 when balloon 16 is deflated. These wings may be desirable for a number of reasons. For example, by including balloon 16 with wings, balloon 16 may have more predictable and consistent re-folding characteristics. Additionally, the wings may be configured so that cutting members 20 can be positioned at the inward-most positions of the deflated balloon 16. This arrangement allows cutting members 20 to be positioned more closely to shaft 18 when balloon 16 is deflated. Accordingly, cutting members 20 can be moved away from the vessel walls where they might otherwise result in contact and, possibly, damage to healthy tissue during movement of catheter 10 within a body lumen. Additionally, alternating the wings and cutting members 20 as well as positioning cutting members 20 relatively close to shaft 18 may allow the wings to fold over and cover cutting members 20 when balloon 16 is deflated. Again, this feature may reduce the exposure of cutting members 20 to the blood vessel.

Balloon 16 additionally may include one or more discrete points or areas of flexibility such as generally circumferentially extending crease 70 formed in the wall of balloon 16. A single crease 70 is shown in FIG. 1; however, two, three, or more creases 70 may be present in balloon 16 to provide a desired flexibility to a distal region of catheter 10. Crease 70 may provide increased flexibility to the distal portion of catheter 10 including balloon 16 during delivery, deployment, and withdrawal of a medical device within a vasculature. Crease 70 may allow balloon 16 having cutting members 20 to readily bend through a curved vascular pathway and maintain conformity to a vessel lumen during inflation of balloon 16 at a target location. Balloons not having such flexibility may tend to straighten as they are inflated in a curved vascular pathway, thereby placing uneven pressure on the wall of the vessel and/or causing unnecessary trauma to the vessel.

Crease 70 may be a circumferential crease, a helical crease, or the like. For example, crease 70 may be disposed substantially orthogonal to cutting member 20 or at an angle thereto. For instance, crease 70 may be formed at a 45-, 60-, 75-, 80- or 90-degree angle relative to cutting member 20. Preferably, crease 70 corresponds with break 46 in cutting member 20. For example, cutting member 20 may be positioned on balloon 16 such that break 46 of cutting member 20 is aligned with crease 70. As shown in FIG. 1, first section 44a may be positioned proximal of crease 70 and second section 44b may be positioned distal of crease 70, such that break 46 is substantially aligned with crease 70.

Crease 70 may be formed in balloon 16 during a molding process, such as a blow molding process, prior to placing cutting members 20 on balloon 16. Alternatively, crease 70 may be formed in balloon 16 during a balloon folding operation subsequent to placing cutting members 20 on balloon 16. A balloon folding fixture may include means for creasing balloon 16, such as notches, ridges, and the like. The balloon 16 may be positioned in a folding fixture such that break 46 of cutting member 20 is aligned with the means for creasing balloon 16. In this process, crease 70 may be fashioned in the balloon 16 during a final folding operation. Alternatively or additionally, crease 70 may be formed by grinding, laser ablating, chemical etching, or ablation and subsequent back fill with a more compliant material, for example.

Crease 70 may be located on the outer surface 40 of balloon 16 or on the inner surface (not shown) of balloon 16. Crease 70 may be a fold created in balloon 16. Alternatively, crease 70 may be defined as a portion of balloon 16 having a reduced wall thickness, a groove, a reduced diameter portion, or recessed area defined in the wall of balloon 16, for example. Crease 70 may also be a portion of balloon 16 comprising a material relatively resistant to expansion. Additionally, crease 70 may be formed by a band of relatively non-expandable material disposed about a portion of balloon 16 or incorporated in a portion of balloon 16. The band of relatively non-expandable material may constrain a portion of balloon 16 from readily expanding to the extent of adjacent regions.

It is also contemplated that balloon 16 may additionally and/or alternatively include at least one crease 70 not aligned with a break 46 in cutting members 20. Such a crease 70 may provide enhanced flexibility along at least a portion of balloon 16. Some further discussion of crease 70 and other examples, features, and modifications are described in more detail below.

Shaft 18 may be a catheter shaft, similar to typical catheter shafts. For example, shaft 18 may include an inner tubular member 24 and outer tubular member 26. Tubular members 24/26 may be manufactured from a number of different materials. For example, tubular members 24/26 may be made of metals, metal alloys, polymers, metal-polymer composites or any other suitable materials. Some examples of suitable metals and metal alloys include stainless steel, such as 300 series stainless steel (including 304V, 304L, and 316L); 400 series martensitic stainless steel; tool steel; nickel-titanium alloy such as linear-elastic or super-elastic Nitinol, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; or other suitable material. Some examples of suitable polymers include those described above in relation to balloon 16. For example, tubular members 24/26 may comprise a reinforced polymer material such as a nano-composite polymer material. Of course, any other polymer or other suitable material including ceramics may be used without departing from the spirit of the invention. The materials used to manufacture inner tubular member 24 may be the same as or be different from the materials used to manufacture outer tubular member 26. Those materials listed herein may also be used for manufacturing other components of catheter 10 including cutting members 20.

Tubular members 24/26 may be arranged in any appropriate way. For example, in some embodiments, inner tubular member 24 can be disposed coaxially within outer tubular member 26. According to these embodiments, inner and outer tubular members 24/26 may or may not be secured to one another along the general longitudinal axis of shaft 18. Alternatively, inner tubular member 24 may follow the inner wall or otherwise be disposed adjacent the inner wall of outer tubular member 26. Again, inner and outer tubular members 24/26 may or may not be secured to one another. For example, inner and outer tubular members 24/26 may be bonded, welded (including tack welding or any other welding technique), or otherwise secured at a bond point. In some embodiments, the bond point may be generally disposed near the distal end of shaft 18. However, one or more bond points may be disposed at any position along shaft 18. The bond may desirably impact, for example, the stability and the ability of tubular members 24/26 to maintain their position relative to one another. In still other embodiments, inner and outer tubular member 24/26 may be adjacent to and substantially parallel to one another so that they are non-overlapping. In these embodiments, shaft 18 may include an outer sheath that is disposed over tubular members 24/26.

Inner tubular member 24 may include an inner lumen 28. In at least some embodiments, inner lumen 28 is a guidewire lumen. Accordingly, catheter 10 can be advanced over guidewire 22 to the desired location. The guidewire lumen may extend along essentially the entire length of catheter shaft 18 so that catheter 10 resembles a traditional "over-the-wire" catheter. Alternatively, the guidewire lumen may extend along only a portion of shaft 18 so that catheter 10 resembles a "single-operator-exchange" or "rapid-exchange" catheter. Regardless of which type of catheter is contemplated, catheter 10 may be configured so that balloon 16 is disposed over at least a region of inner lumen 28. In at least some of these embodiments, inner lumen 28 (i.e., the portion of inner lumen 28 that balloon 16 is disposed over) may be substantially coaxial with balloon 16.

Shaft 18 may also include an inflation lumen 30 that may be used, for example, to transport inflation media to and from balloon 16. The location and position of inflation lumen 30 may vary, depending on the configuration of tubular members 24/26. For example, when outer tubular member 26 is disposed over inner tubular member 24, inflation lumen 30 may be defined within the space between tubular members 24/26. Moreover, depending on the position of inner tubular member 24 within outer tubular member 26, the shape of lumen 30 (i.e., the shape adjacent shaft 18) may vary. For example, if inner tubular member 24 is attached to or disposed adjacent to the inside surface of outer tubular member 26, then inflation lumen 30 may be generally half-moon in shape; whereas, if inner tubular member 24 is generally coaxial with outer tubular member 26, then inflation lumen 30 may be generally ring-shaped or annular in shape. It can be appreciated that if outer tubular member 26 is disposed alongside inner tubular member 24, then lumen 30 may be the lumen of outer tubular member 26 or it may be the space defined between the outer surface of tubular members 24/26 and the outer sheath disposed thereover.

Balloon 16 may be coupled to catheter shaft 18 in any of a number of suitable ways. For example, balloon 16 may be adhesively or thermally bonded to shaft 18. Such bonding techniques may include laser welding, heat shrinking, adhesive, and tie layers, for example. In some embodiments, a proximal waist 32 of balloon 16 may be bonded to shaft 18, for example, at outer tubular member 26, and a distal waist 34 may be bonded to shaft 18, for example, at inner tubular member 24. The exact bonding positions, however, may vary. It can be appreciated that a section of proximal waist 32 may not have sections 36 extending therefrom in order for suitable bonding between balloon 16 and outer tubular member 30.

In addition to some of the structures described above, shaft 18 may also include a number of other structural elements, including those typically associated with catheter shafts. For example, shaft 18 may include a radiopaque marker coupled thereto that may aid a user in determining the location of catheter 10 within the vasculature. In addition, catheter 10 may include a folding spring (not shown) coupled to balloon 16, for example, adjacent proximal waist 32, which may further help in balloon folding and refolding. A description of a suitable folding spring can be found in U.S. Pat. No. 6,425,882, the disclosure of which is incorporated herein by reference.

Figure 2:
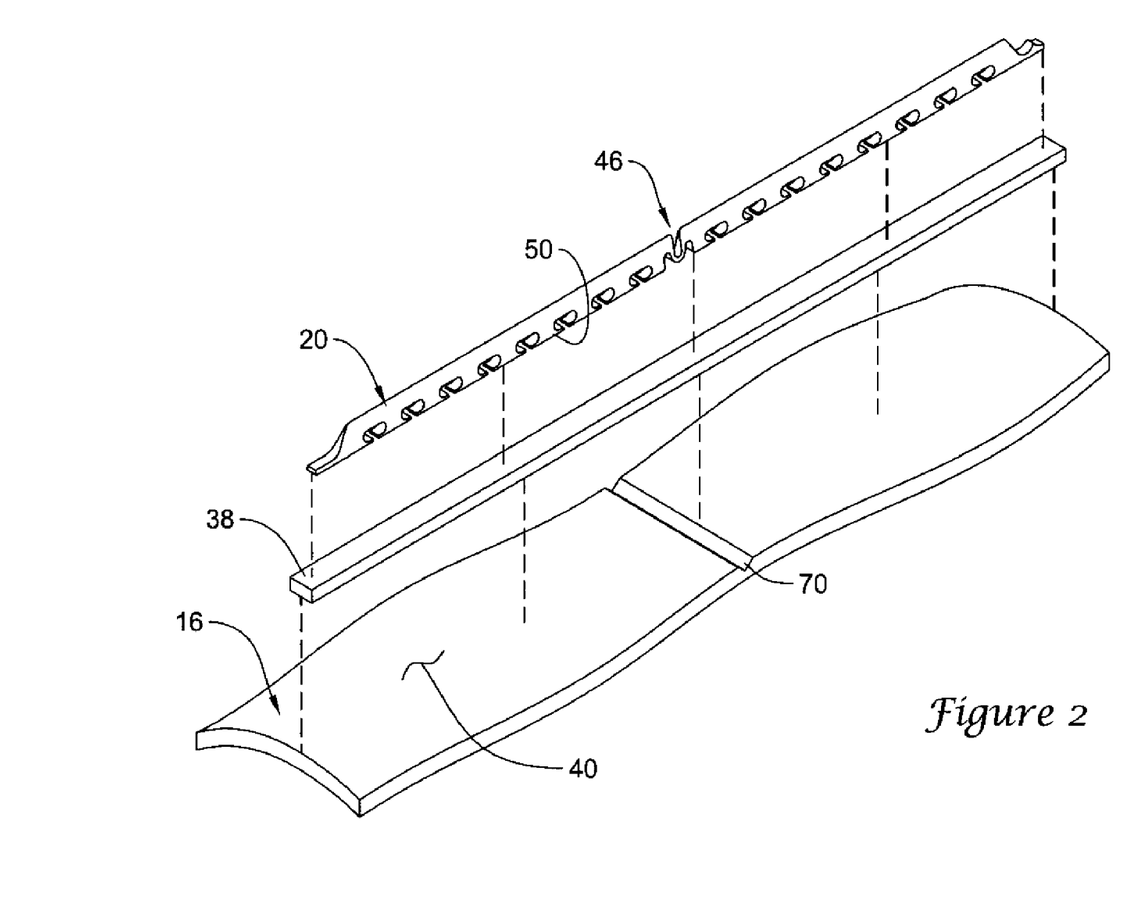
FIG. 2 is a partial perspective view of a representative cutting member and balloon having at least one generally circumferentially extending crease in accordance with an embodiment of the invention.

An exploded view illustrating the attachment of cutting member 20 to balloon 16 is shown in FIG. 2. Here it can be seen that a joining member or polymeric strip 38 may be coupled to cutting member 20 and to balloon 16. Joining member 38 may be formed from a generally flexible or soft material that allows the interface between cutting member 20 and balloon 16 to be somewhat elastic or pliable. For example, joining member 38 may be manufactured from a low durometer polyurethane or any other suitable material (including any of the polymers and other materials disclosed herein). Accordingly, cutting member 20 may be securely coupled to balloon 16 while still being able to move laterally about eight degrees or less. In addition, different portions of cutting member 20 may be able to bend or flex, while other portions remain essentially unchanged.

In at least some embodiments, joining member 38 may be attached to and disposed between cutting member 20 and balloon 16. For example, joining member 38 may be attached to an outer surface 40 of balloon 16 and to a base 50 of the cutting member 20. The attachment of joining member 38 with cutting member 20 and balloon 16 may be achieved in any appropriate manner, such as by adhesive bonding, casting, thermal bonding, mechanically connecting, welding, brazing, and the like, or in any other suitable way. The attachment means need not be the same for the attachment between cutting member 20 and joining member 38 as the means used to attach balloon 16 and joining member 38.

Balloon 16 may include a discrete region of flexibility such as crease 70 formed in the outer surface 40 of balloon 16. Break 46 of cutting member 20 may be aligned with crease 70 such that the increased flexibility of balloon 16 provided by crease 70 may be combined with the increased flexibility of cutting member 20 provided by break 46. The enhanced flexibility of balloon 16 may improve the deliverability of the catheter, as well as the conformity of balloon 16 to a vessel lumen curvature during inflation of balloon 16.

Figure 3:
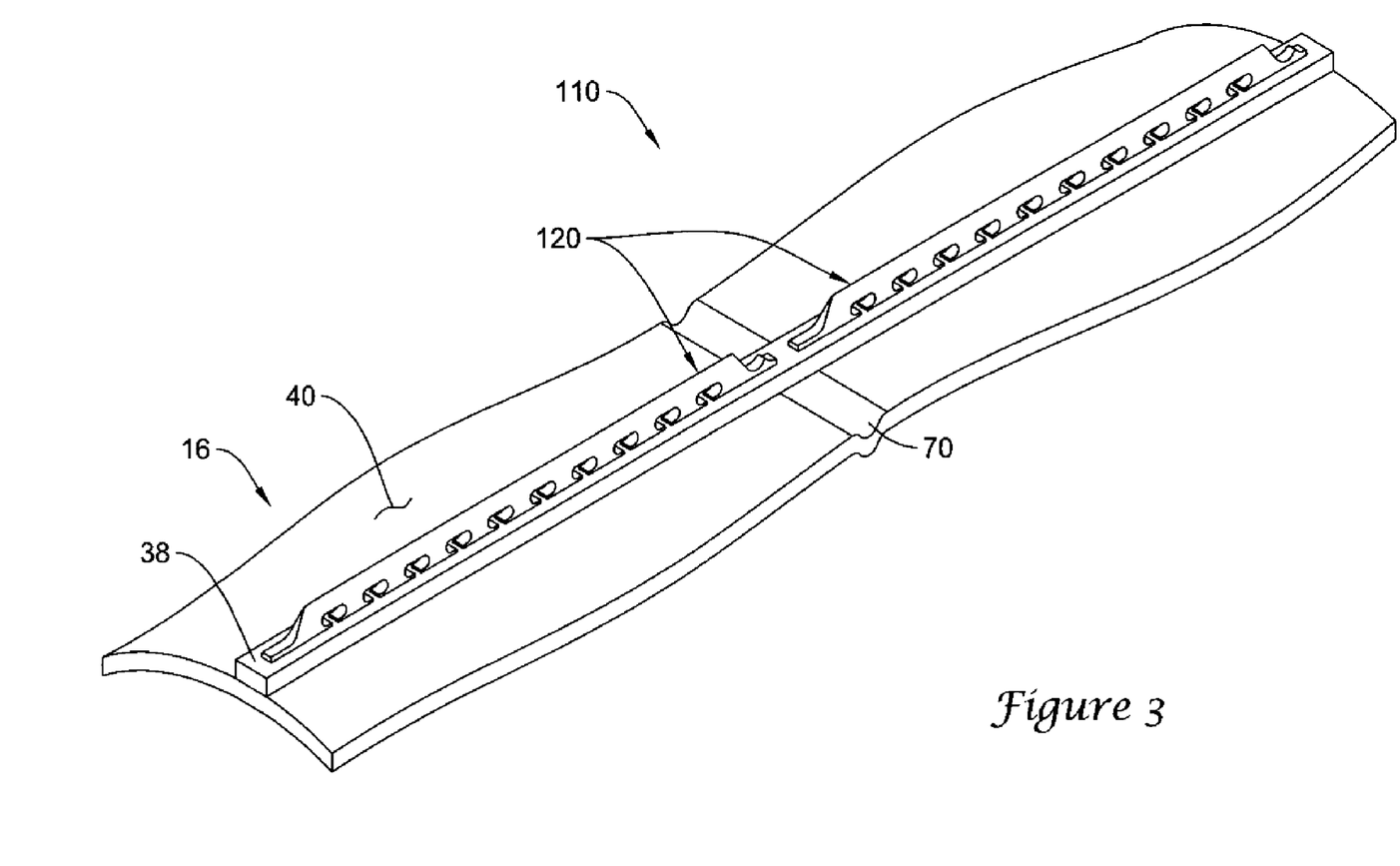
FIG. 3 is a partial perspective view of another representative cutting member and balloon having at least one generally circumferentially extending crease in accordance with an embodiment of the invention.

FIG. 3 depicts a partial perspective view of another catheter 110 that is similar to catheter 10. Catheter 110 includes cutting members 120 disposed about balloon 16 in a tandem arrangement. In other words, two cutting members 120 may be arranged end-to-end to define an elongated cutting surface. This embodiment may increase the flexibility of cutting members 120 by dividing what might otherwise be a single cutting blade into multiple discrete sections. Thus, the cutting members 120 may individually have a shortened length, making balloon 16 more amenable to bending or flexing. It can be appreciated that the precise arrangement of cutting members 120 is not intended to be limited to a tandem configuration. For example, cutting members 120 may have an arrangement that is longitudinally offset. Additionally, catheter 110 is not limited to pairs of cutting members 120, as any suitable number of cutting members 120 may be used without departing from the spirit of the invention.

It can also be seen in FIG. 3 that cutting members 120 may be positioned on either side of crease 70 in balloon 16. As illustrated in this embodiment, crease 70 may be a reduced diameter portion or material offset of balloon 16. Crease 70 provides increased flexibility to the balloon 16. Placing cutting members 120 on either side of crease 70 provides flexibility to the balloon 16 while maintaining sufficient functionality of balloon 16 necessary to perform a medical procedure at a target location. Joining member 38 may extend over crease 70, or joining member 38 may terminate proximate crease 70. Alternatively, joining member 38 may be absent from catheter assembly 110.

Figure 4:
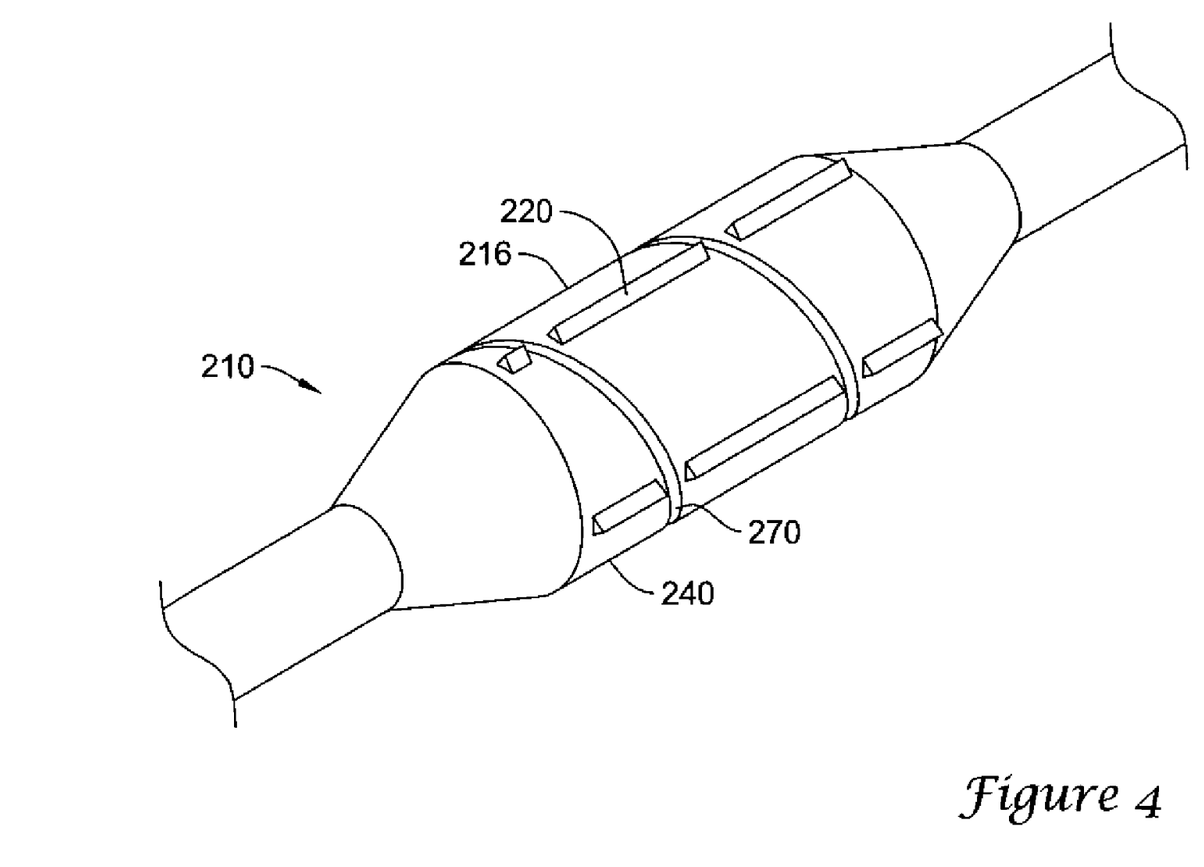
FIG. 4 is a partial perspective view of a representative cutting balloon catheter including a balloon having at least one crease in accordance with an embodiment of the invention.

FIG. 4 depicts a perspective view of a catheter 210 similar to catheter 10. Catheter 210 includes a balloon 216 disposed about a distal region of catheter 210. Balloon 216 includes a helical crease 270 disposed about the outer surface 240 of balloon 216. Cutting members 220 may be arranged about balloon 216 such that cutting members 220 are coupled away from crease 270. In other words, cutting members 220 are positioned such that they do not extend over helical crease 270. Alternately, cutting members 220 may extend substantially the length of balloon 216, thereby traversing crease 270. Helical crease 270 may provide increased flexibility of the balloon 216 during a medical procedure.

Figure 5:
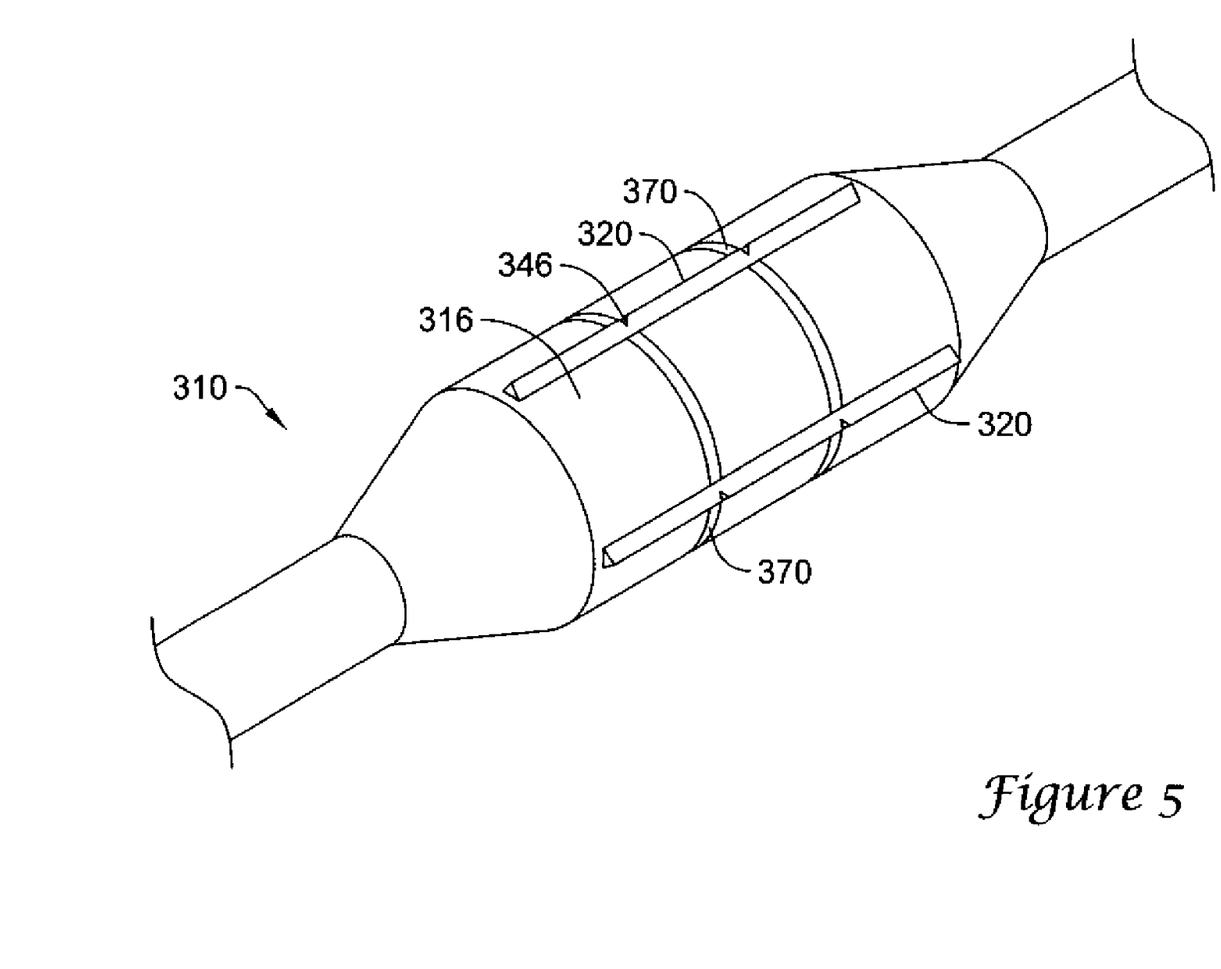
FIG. 5 is a partial perspective view of another representative cutting balloon catheter including a balloon having at least one crease in accordance with an embodiment of the invention.

FIG. 5 is a perspective view of a catheter 310 similar to catheter 10. Balloon 316 may include a plurality of creases 370. As shown in FIG. 5, balloon 316 may include two creases 370 extending around the circumference of balloon 316. However, it should be recognized that balloon 316 may include additional creases 370. A plurality of cutting members 320 may be coupled to the balloon 316. Preferably, cutting members 320 are coupled equidistantly about balloon 316. Cutting member 320 may extend substantially the length of balloon 316 or a portion thereof. As shown in FIG. 5, cutting member 320 may include a plurality of integral segments separated with a break 346 therebetween. Each cutting member 320 is positioned such that break 346 is aligned with crease 370. In other words, cutting member 320 may be positioned such that break 346 is located at the same longitudinal position along balloon 316 as crease 370. Aligning break 346 with crease 370 provides balloon 316 with defined flexibility regions along its length.

Figure 6:
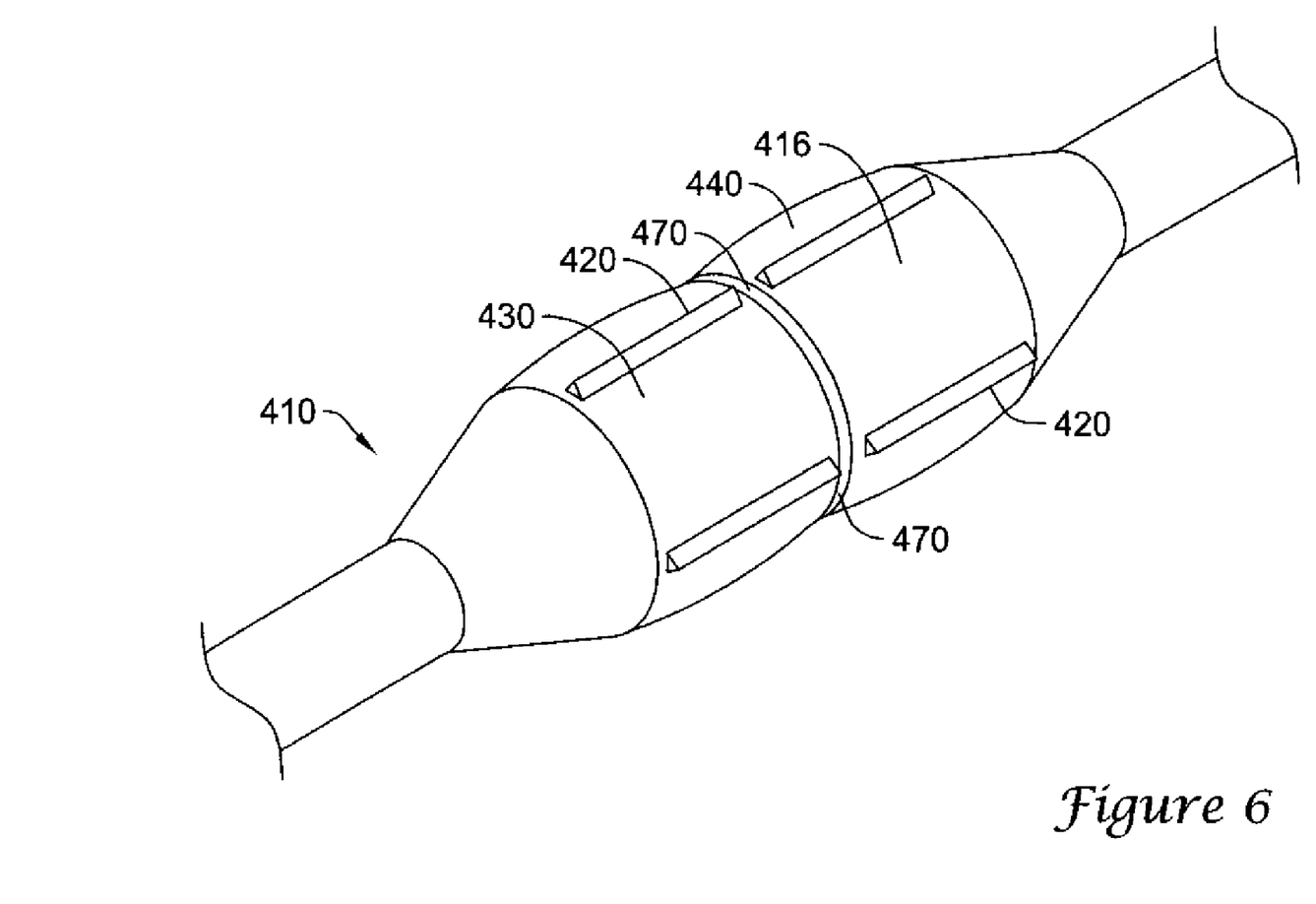
FIG. 6 is a partial perspective view of another representative cutting balloon catheter including a balloon having at least one crease in accordance with an embodiment of the invention.

FIG. 6 depicts a perspective view of catheter 410 similar to catheter 10. Catheter 410 includes an expandable member 416 including at least one crease 470. Crease 470 may be a portion of expandable member 416 having a reduced diameter relative to proximal balloon section 430 and distal balloon section 440. A plurality of cutting members 420 may be coupled to balloon 416. Each cutting member 420 may extend along substantially the length of proximal section 430 or distal section 440, thereby leaving crease 470 free of cutting members 420. Therefore, a flexibility region may be formed at crease 470 to impart greater flexibility in balloon 416.

Figure 7:
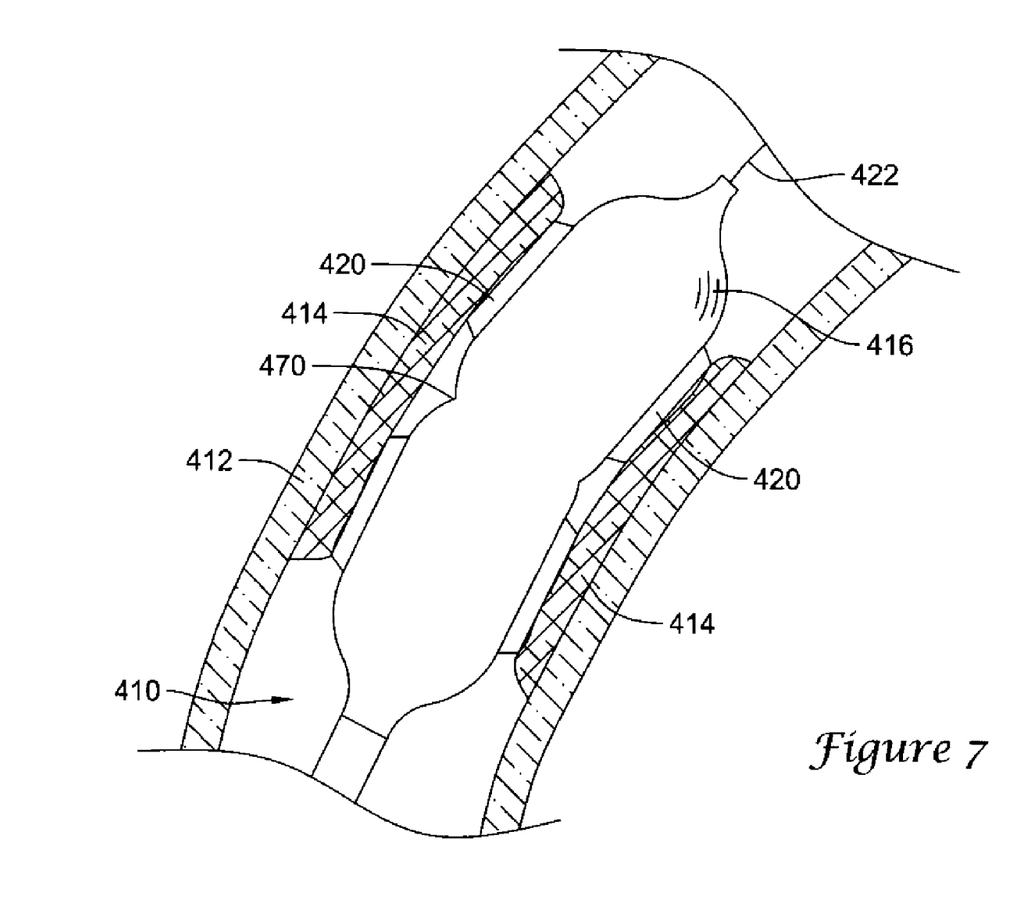
FIG. 7 is a partial cross-sectional view of a representative cutting balloon catheter disposed in a curved vasculature.

FIG. 7 shows a representative catheter disposed in a vessel having a curved profile. Catheter 410 is shown in FIG. 7; however, catheter 410 may be replaced with other representative embodiments or any combination thereof disclosed herein. Catheter 410 may be advanced through the vasculature over guidewire 422 until expandable member 416 reaches a target location such as stenosis 414. Stenosis 414 may be located in a curved portion of vessel 412. As expandable member 416 is expanded, cutting members 420 may contact stenosis 414. Crease 470 allows expandable member 416 to maintain a curved profile while being expanded. Therefore, cutting members 420 may contact stenosis 414 along a longer portion of the curved region, reducing trauma to the vessel 412 and/or minimizing the need for additional procedures. Additionally, pressure within expandable member 416 may be more evenly transmitted throughout expandable member 416 when expandable member 416 conforms to the curvature of vessel 412 attributable at least in part to crease 470. Therefore, cutting members 420 may contact stenosis 414 more uniformly and along a longer portion of their length.

Figure 8:
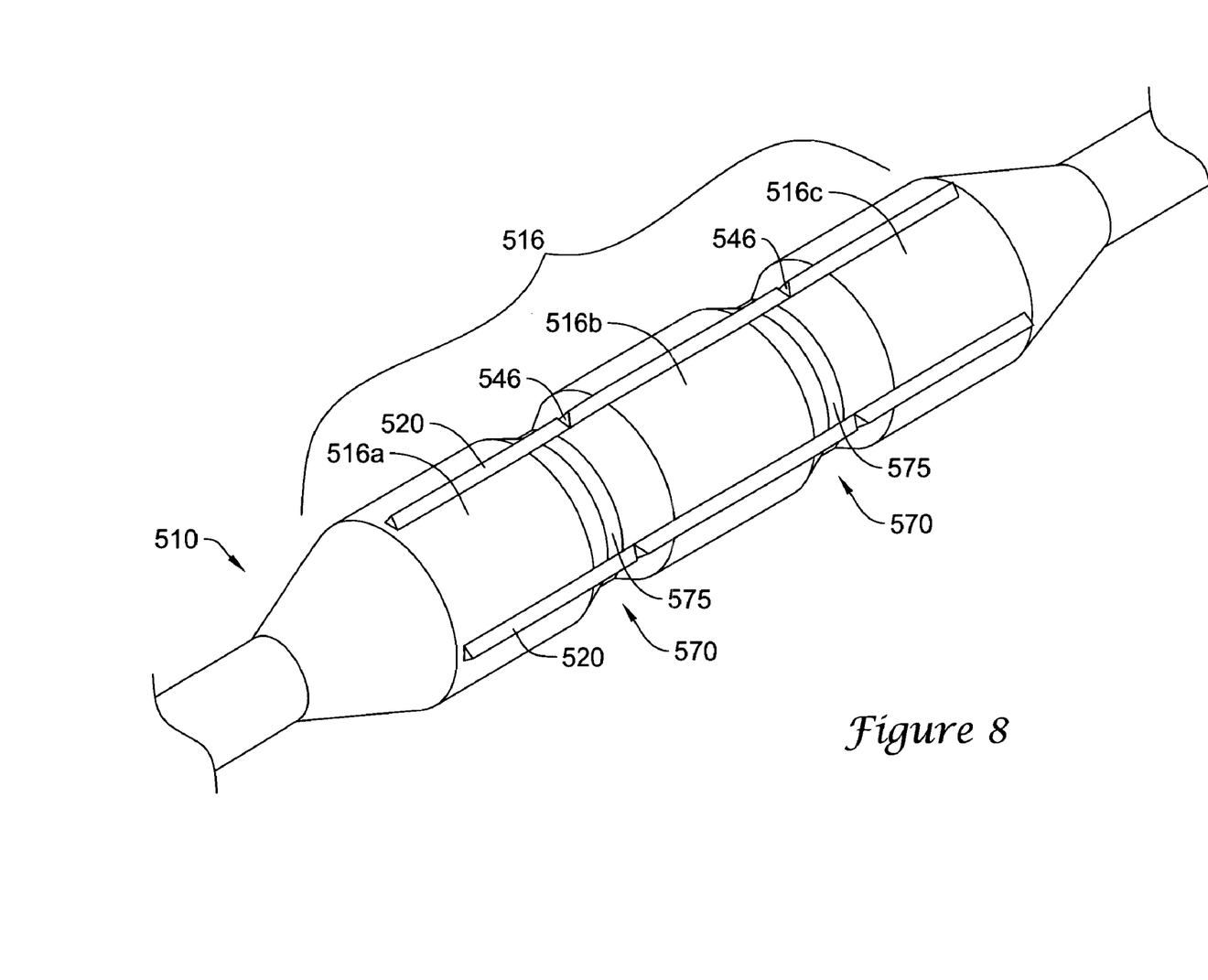
FIG. 8 is a partial perspective view of another representative cutting balloon catheter including a multi-lobed balloon.

FIG. 8 shows a catheter 510 including a multi-lobed balloon 516. Multi-lobed balloon 516 includes three segments or lobes 516a, 516b, 516c. However, balloon 516 may include two, three, four, five, six or more lobes. Multi-lobed balloon 516 may be coupled to a distal portion of catheter 510. Lobes may be formed in balloon 516 in a variety of ways. For example, a band 575 may be disposed about a portion of balloon 516 restraining a portion of balloon 516 from expanding, thereby allowing a portion of balloon 516 to expand while constraining an adjacent portion by band 575. Band 575 may be a discrete, relatively non-expandable member disposed about a portion of balloon 516. Instead, balloon may be made of a material having alternating portions. For example band 575 may be a portion of balloon 516 including a relatively non-expandable material while lobes 516a, 516b, 516c may include a relatively expandable material. Alternatively or additionally, band 575 may be a portion of balloon 516 of a greater thickness than adjacent lobes 516a, 516b, 516c. Portions of material of a greater thickness may not expand as readily as adjacent areas having a thinner thickness, thereby allowing lobes 516a, 516b, 516c to expand while band 575 retains a reduced cross-sectioned profile.

One or more cutting members 520 may be coupled to balloon 516. As shown in FIG. 8, the one or more cutting members 520 may extend substantially the length of balloon 516. Alternatively, cutting members 520 may individually be coupled to one of lobes 516a, 516b, 516c, therefore not extending over a reduced cross-sectioned region 570. Cutting members 520 may include one or more flexibility regions or breaks 546 for increased flexibility. Preferably, break 546 in cutting member 520 may be aligned with reduced cross-sectioned region 570 to impart enhanced flexibility to catheter 510. In other words, cutting member 520 may be positioned such that break 546 is located at the same longitudinal position of balloon 516 as band 575. Such an arrangement may provide catheter 510 with sufficient flexibility to navigate a tortuous vasculature and retain a curved configuration during inflation of balloon 516 at a target location.

Figure 9:
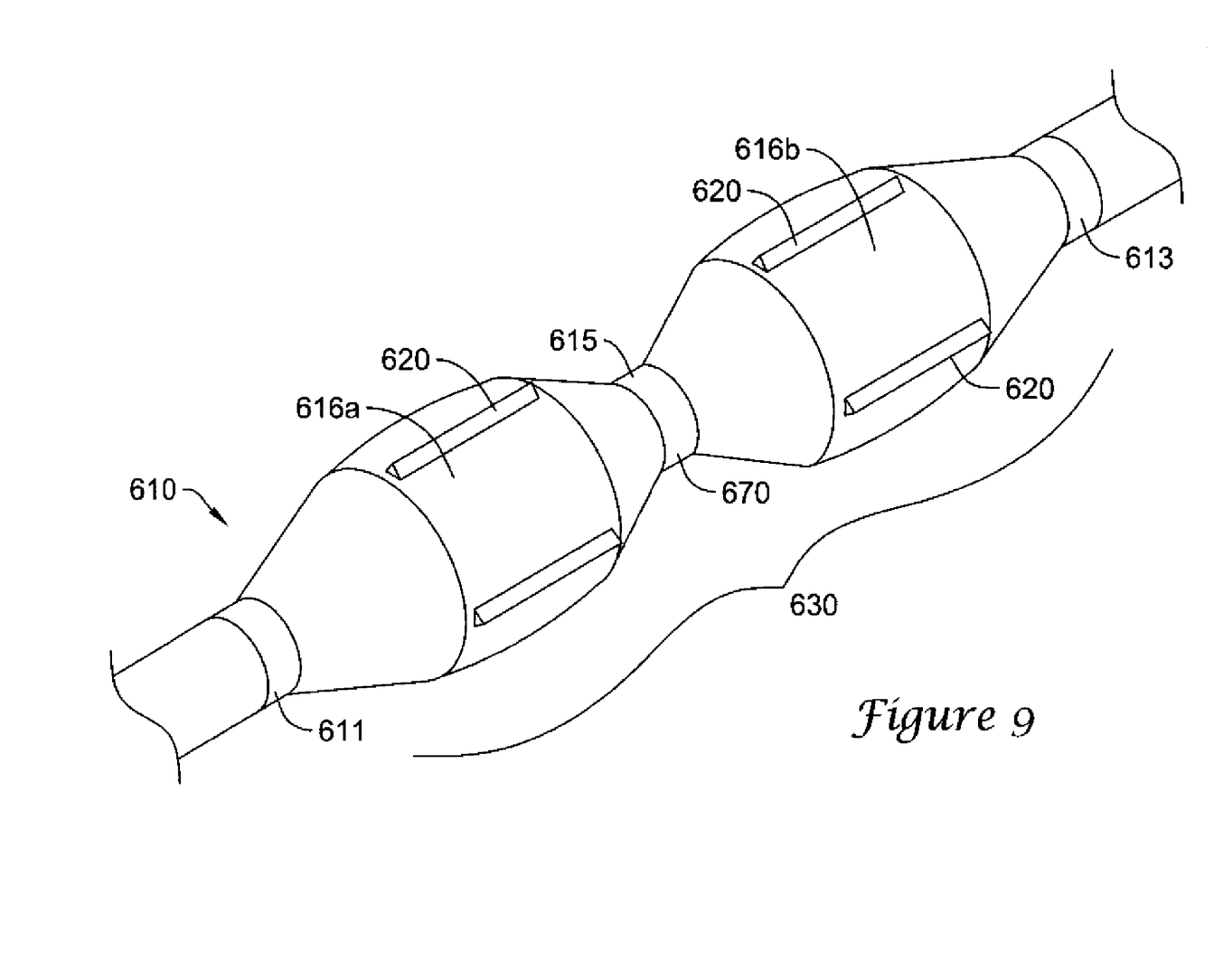
FIG. 9 is a partial perspective view of another representative cutting balloon catheter including a plurality of expandable balloons.

FIG. 9 shows a catheter 610 having a distal portion 630 including a plurality of balloons 616a, 616b. Although FIG. 9 shows a catheter 610 having two balloons 616a, 616b, it is contemplated that catheter 610 may include two, three, four, five, six or more balloons 616. Proximal balloon 616a may be secured to catheter 610 at proximal waist 611 and intermediate waist 615. Distal balloon 616b may be secured to catheter 610 at distal waist 613 and intermediate waist 615. Intermediate waist 615 may be a portion of proximal balloon 616a, distal balloon 616b, or intermediate waist 615 may be a portion shared with proximal balloon 616a and distal balloon 616b. Balloon 616a may be integrally connected with balloon 616b by intermediate waist 615. Intermediate waist 615 may be secured to catheter 610 in any of a number of suitable ways. For example, intermediate waist 615 may be adhesively or thermally bonded to catheter 610, or intermediate waist 615 may be secured to catheter 610 by a discrete member such as a heat shrink tube, coupler, generally inelastic member, or the like. Such bonding techniques may include laser welding, heat shrinking, adhesive, and tie layers, for example. Alternatively, balloons 616a, 616b may comprise two discrete elements each having an intermediate waist 615 secured to catheter 610. Balloons 616a, 616b may be independently expanded, expanded simultaneously, or expanded in series.

A plurality of cutting members 620 may be coupled to balloons 616a, 616b. Preferably, each balloon 616a, 616b may include three cutting members 620 disposed equidistantly about balloon 616a, 616b. However, each balloon 616a, 616b may include one, two, three, four, five, six or more cutting members 620.

Intermediate waist 615 may define a reduced cross-sectioned region 670 of distal portion 630 of catheter 610 while balloons 616a, 616b are expanded. Therefore, reduced cross-sectioned region 670 may provide a discrete point of flexibility in the distal region 630 of catheter 610. In an expanded state, the distal region 630 of catheter 610 may readily conform to the curvature of a vessel due to a discrete point of flexibility 670 provided by intermediate waist 615. The enhanced flexibility of distal portion 630 may allow expansion of balloons 616a, 616b within a vessel without surrendering compliance to a curvature of a vessel. Therefore, catheter 610 may be designed to sufficiently treat a stenosis located in a sharply curved portion of a vessel.

Those skilled in the art will recognize that the present invention may be manifested in a variety of forms other than the specific embodiments described and contemplated herein. It is contemplated that one may combine, substitute, or modify specific elements of the various embodiments described herein without departing from the scope and spirit of the invention. Accordingly, departure in form and detail may be made without departing from the scope and spirit of the present invention as described in the appended claims.

What is claimed is:
1. A medical device comprising:
an elongate shaft having a distal region;

an expandable member coupled to the distal region of the elongate shaft;

one or more monolithic cutting members coupled to the expandable member, wherein at least one of the monolithic cutting members includes a cutting surface, and wherein a notch is formed in the cutting surface, the notch extending radially inward from the cutting surface toward the expandable member only partially through the monolithic cutting member and defines defining two or more longitudinally-aligned blade segments; and wherein the expandable member includes at least one generally circumferential crease that is aligned with the notch.

2. The medical device of claim 1, wherein the expandable member includes a relatively non-compliant material.

3. The medical device of claim 1, wherein the one or more creases are a recessed area of the expandable member.

4. The medical device of claim 1, wherein the one or more creases are a reduced diameter portion of the expandable member.

5. The medical device of claim 1, wherein the one or more cutting members traverse the one or more circumferential creases.

6. The medical device of claim 1, wherein the one or more circumferential creases are orthogonal to the one or more cutting members.

7. A cutting balloon catheter, comprising:
a catheter shaft having a distal region;
a balloon coupled to the distal region of the catheter shaft;
wherein a crease is formed in the balloon that extends about the balloon; and
a single, unitary cutting blade attached to the balloon, wherein the cutting blade has a notch formed therein, the notch extending from a cutting surface of the cutting blade toward a longitudinal axis of the balloon and extending only partially through the cutting blade;
wherein the notch longitudinally aligns with the crease at a common longitudinal position along the axis.

8. The cutting balloon catheter of claim 7, wherein the crease includes a recessed area of the balloon.

9. The cutting balloon catheter of claim 7, wherein the crease includes a reduced diameter portion of the balloon.

10. The cutting balloon catheter of claim 7, wherein the cutting blade is substantially orthogonal to the crease.

11. The cutting balloon catheter of claim 7, wherein the balloon includes a second crease that extends about the balloon.

12. The cutting balloon catheter of claim 11, wherein the cutting blade includes a second notch, and wherein the second notch is aligned with the second crease.

13. The cutting balloon catheter of claim 12, further comprising a second cutting blade attached to the balloon.

14. The cutting balloon catheter of claim 13, wherein the second cutting blade includes a third notch and a fourth notch, wherein the third notch is aligned with the crease, and wherein the fourth notch is aligned with the second crease.

15. The cutting balloon catheter of claim 14, further comprising one or more additional cutting blades.

16. The cutting balloon catheter of claim 7, wherein the cutting blade is attached to the balloon with a joining member.

17. The cutting balloon catheter of claim 7, further comprising one or more additional cutting blades.

18. A cutting balloon catheter, comprising:
a catheter shaft having a distal region and a longitudinal axis;
a balloon coupled to the distal region of the catheter shaft;
wherein the balloon has a circumferential groove formed therein; and
a cutting blade attached to the balloon by an intermediate joining member, wherein the cutting blade has a cutting surface and a notch formed in the cutting surface that extends only partially through the cutting blade toward the balloon, the notch being aligned with the circumferential groove at the same longitudinal position along the axis.

19. The cutting balloon catheter of claim 18, wherein the balloon includes a second circumferential groove.

20. The cutting balloon catheter of claim 19, wherein the cutting blade includes a second notch, and wherein the second notch is aligned with the second circumferential groove.

* * * * *